United States Patent
Shaiken

(10) Patent No.: US 11,428,693 B2
(45) Date of Patent: Aug. 30, 2022

(54) METHOD OF HIGH THROUGHPUT SCREENING OF CHEMICAL COMPOUNDS SUPPRESSING NUCLEOLAR HYPERTROPHY

(71) Applicant: Baylor College of Medicine, Houston, TX (US)

(72) Inventor: Tattym E. Shaiken, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 609 days.

(21) Appl. No.: 16/491,566

(22) PCT Filed: Feb. 15, 2018

(86) PCT No.: PCT/US2018/018435
§ 371 (c)(1),
(2) Date: Sep. 5, 2019

(87) PCT Pub. No.: WO2018/169644
PCT Pub. Date: Sep. 20, 2018

(65) Prior Publication Data
US 2021/0140968 A1     May 13, 2021

Related U.S. Application Data

(60) Provisional application No. 62/472,066, filed on Mar. 16, 2017.

(51) Int. Cl.
*G01N 33/574* (2006.01)
*G01N 33/50* (2006.01)

(52) U.S. Cl.
CPC ... *G01N 33/57496* (2013.01); *G01N 33/5011* (2013.01); *G01N 33/5017* (2013.01); *G01N 33/5026* (2013.01); *G01N 33/5035* (2013.01); *G01N 33/5076* (2013.01)

(58) Field of Classification Search
CPC ......... G01N 33/57497; G01N 33/5017; G01N 33/5026; G01N 33/5076; G01N 33/5035; G01N 33/5011
See application file for complete search history.

(56) References Cited

U.S. PATENT DOCUMENTS

2006/0094868 A1   5/2006   Giuliano et al.
2009/0317836 A1   12/2009  Kuhn et al.

OTHER PUBLICATIONS

Neumuller et al (ScienceSignaling.Org (2013); 6(289)ra70 (15 pages).*
ISA/US, International Search Report/Written Opinion for PCT/US18/18435, dated May 1, 2018, 6 pages.
Matsumoto et al., "Loss of the integral nuclear envelope protein SUN1 induces alteration of nucleoli", Nucleus, 2016, vol. 7:1, pp. 68-83.
Pickard et al., "The Cell's Nucleolus: an Emerging Target for Chemotherapeutic Intervention", ChemMedChem, 2013, vol. 8. 37 pages.
Quin, et al. "Targeting the nucleolus for cancer intervention", Biochimica et Biophysica Acta, 2014, vol. 1842, pp. 802-816.

* cited by examiner

*Primary Examiner* — Shirley V Gembeh
(74) *Attorney, Agent, or Firm* — William R. Childs; Childs Law

(57) ABSTRACT

The present disclosure relates to methods for screening test samples or substances that are capable of inducing or reducing nucleolar hypertrophy in cancer cells. The present disclosure further provides methods of contacting isolated cancer cells with a test sample or a substance that can induce nucleolar hypertrophy in a cancer cell. The present disclosure further provides methods for contacting an isolated cancer cell characterized by nucleolar hypertrophy with a test sample or substance that can reduce the nucleolar hypertrophy. One benefit to the method of screening disclosed herein can be the identification of test samples or substances capable of reducing nucleolar hypertrophy. Another benefit to the method of screening disclosed herein can be the identification of those combinations of test samples, substances, or combinations or series thereof, which are suitable or optimal for treating specific cancers in patients.

15 Claims, 11 Drawing Sheets

FIG. 9

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | C | C | x1 | x1 | x2 | x2 | x3 | x3 | x4 | x4 | x5 | x5 | x6 | x6 | x7 | x7 | x8 | x8 | x9 | x9 | x10 | x10 | x11 | x11 |
| B | C | C | x1 | x1 | x2 | x2 | x3 | x3 | x4 | x4 | x5 | x5 | x6 | x6 | x7 | x7 | x8 | x8 | x9 | x9 | x10 | x10 | x11 | x11 |
| C | x12 | x12 | x13 | x13 | x14 | x14 | x15 | x15 | x16 | x16 | x17 | x17 | x18 | x18 | x19 | x19 | x20 | x20 | x21 | x21 | x22 | x22 | x23 | x23 |
| D | x12 | x12 | x13 | x13 | x14 | x14 | x15 | x15 | x16 | x16 | x17 | x17 | x18 | x18 | x19 | x19 | x20 | x20 | x21 | x21 | x22 | x22 | x23 | x23 |
| E | x24 | x24 | x25 | x25 | x26 | x26 | x27 | x27 | x28 | x28 | x29 | x29 | x30 | x30 | x31 | x31 | x32 | x32 | x33 | x33 | x34 | x34 | x35 | x35 |
| F | x24 | x24 | x25 | x25 | x26 | x26 | x27 | x27 | x28 | x28 | x29 | x29 | x30 | x30 | x31 | x31 | x32 | x32 | x33 | x33 | x34 | x34 | x35 | x35 |
| G | x36 | x36 | x37 | x37 | x38 | x38 | x39 | x39 | x40 | x40 | x41 | x41 | x42 | x42 | x43 | x43 | x44 | x44 | x45 | x45 | x46 | x46 | x47 | x47 |
| H | x36 | x36 | x37 | x37 | x38 | x38 | x39 | x39 | x40 | x40 | x41 | x41 | x42 | x42 | x43 | x43 | x44 | x44 | x45 | x45 | x46 | x46 | x47 | x47 |
| I | y | y | yx1 | yx1 | yx2 | yx2 | yx3 | yx3 | yx4 | yx4 | yx5 | yx5 | yx6 | yx6 | yx7 | yx7 | yx8 | yx8 | yx9 | yx9 | yx10 | yx10 | yx11 | yx11 |
| J | y | y | yx1 | yx1 | yx2 | yx2 | yx3 | yx3 | yx4 | yx4 | yx5 | yx5 | yx6 | yx6 | yx7 | yx7 | yx8 | yx8 | yx9 | yx9 | yx10 | yx10 | yx11 | yx11 |
| K | yx12 | yx12 | yx13 | yx13 | yx14 | yx14 | yx15 | yx15 | yx16 | yx16 | yx17 | yx17 | yx18 | yx18 | yx19 | yx19 | yx20 | yx20 | yx21 | yx21 | yx22 | yx22 | yx23 | yx23 |
| L | yx12 | yx12 | yx13 | yx13 | yx14 | yx14 | yx15 | yx15 | yx16 | yx16 | yx17 | yx17 | yx18 | yx18 | yx19 | yx19 | yx20 | yx20 | yx21 | yx21 | yx22 | yx22 | yx23 | yx23 |
| M | yx24 | yx24 | yx25 | yx25 | yx26 | yx26 | yx27 | yx27 | yx28 | yx28 | yx29 | yx29 | yx30 | yx30 | yx31 | yx31 | yx32 | yx32 | yx33 | yx33 | yx34 | yx34 | yx35 | yx35 |
| N | yx24 | yx24 | yx25 | yx25 | yx26 | yx26 | yx27 | yx27 | yx28 | yx28 | yx29 | yx29 | yx30 | yx30 | yx31 | yx31 | yx32 | yx32 | yx33 | yx33 | yx34 | yx34 | yx35 | yx35 |
| O | yx36 | yx36 | yx37 | yx37 | yx38 | yx38 | yx39 | yx39 | yx40 | yx40 | yx41 | yx41 | yx42 | yx42 | yx43 | yx43 | yx44 | yx44 | yx45 | yx45 | yx46 | yx46 | yx47 | yx47 |
| P | yx36 | yx36 | yx37 | yx37 | yx38 | yx38 | yx39 | yx39 | yx40 | yx40 | yx41 | yx41 | yx42 | yx42 | yx43 | yx43 | yx44 | yx44 | yx45 | yx45 | yx46 | yx46 | yx47 | yx47 |

METHOD OF HIGH THROUGHPUT SCREENING OF CHEMICAL COMPOUNDS SUPPRESSING NUCLEOLAR HYPERTROPHY

CROSS-REFERENCE TO RELATED APPLICATIONS

This application claims the benefit of U.S. Provisional Application No. 62/472,066, which was filed on Mar. 16, 2017, the entire contents of which is hereby incorporated by reference herein.

TECHNICAL FIELD

The present disclosure relates to methods for screening test samples or substances that are capable of inducing or reducing nucleolar hypertrophy in cancer cells. The present disclosure further provides methods of contacting isolated cancer cells with a test sample or a substance that can induce nucleolar hypertrophy in a cancer cell. The present disclosure further provides methods for contacting an isolated cancer cell characterized by nucleolar hypertrophy with a test sample or substance that can reduce the nucleolar hypertrophy. One benefit to the method of screening disclosed herein can be the identification of test samples or substances capable of reducing nucleolar hypertrophy. Another benefit to the method of screening disclosed herein can be the identification of those combinations of test samples, substances, or combinations or series thereof, which are suitable or optimal for treating specific cancers in patients.

BACKGROUND

Many drugs have been approved for the treatment of cancer in patients. However, two great challenges face modern researchers: cancer heterogeneity and drug resistance. Cancer or tumor heterogeneity is the acknowledgement that not all of the cancer cells within a patient are the same. A patient may have different cancer cells from one tumor to another or within a single tumor. Cancer heterogeneity can result in treatments that are highly effective for one group of cancer cells, but less effective or ineffective for another, leading to selective growth of the drug resistant cancer cells.

This challenge has recently given rise to the field of individualized anticancer medicine. Non-individualized anticancer medicine can be described a "trial and error" method or a "shotgun" approach, where a medical care provider proscribes an anticancer drug or regimen on a trial and error basis to determine the reaction of cancerous tumors to the treatment. In contrast, individualized anticancer medicine proposes to test each tumor or patient for those specific treatments or treatment regimens which are most effective for each patient or tumor. There are many challenges associated with how this ideal can become a reality.

The second challenge is associated with a drug resistance that does appears to develop during treatment, instead of being based on cancer heterogeneity. This second challenge often stops or reduces the efficacy of even the most promising treatments.

There is a need to determine which substances can reduce the drug resistance of cellular proliferative disorders, including cancer.

SUMMARY

A method for screening a cancer cell of a human subject for a nucleolar hypertrophy reducing agent is disclosed. In an embodiment, the method includes: contacting an isolated cancer cell characterized by nucleolar hypertrophy with a first test sample; and determining if the first test sample reduces the nucleolar hypertrophy in the isolated cancer cell. In an embodiment, the step of determining if the first test sample reduces the nucleolar hypertrophy in the isolated cancer cell includes: measuring at least one of a decrease in a number of nucleoli, a number of nucleoli-containing nuclei, and a number of nucleoli per nucleus in the isolated cancer cell relative to the isolated cancer cell characterized by nucleolar hypertrophy before contact with the first test sample. In an embodiment, the step of determining if the first test sample reduces the nucleolar hypertrophy in the isolated cancer cell includes: measuring at least one of a decrease in a number of nucleoli, a number of nucleoli-containing nuclei, and a number of nucleoli per nucleus relative to a control isolated cancer cell characterized by nucleolar hypertrophy.

In an embodiment of the method, the method further includes screening the cancer cell of the human subject for a nucleolar hypertrophy inducing agent including: contacting the isolated cancer cell with a second test sample; and determining if the second test sample induces nucleolar hypertrophy in the isolated cancer cell. In an embodiment, the step of determining if the second test sample induces nucleolar hypertrophy in the isolated cancer cell includes: measuring at least one of an increase in a number of nucleoli, a number of nucleoli-containing nuclei, and a number of nucleoli per nucleus in the isolated cancer cell relative to the isolated cancer cell before contact with second test sample. In an embodiment, the step of determining if the second test sample induces nucleolar hypertrophy in the isolated cancer cell includes: measuring at least one of an increase in a number of nucleoli, a number of nucleoli-containing nuclei, and a number of nucleoli per nucleus in the isolated cancer cell relative to a control isolated cancer cell.

In an embodiment of the method, the first test sample includes an FDA approved drug, a natural product, an alkaloid, a monoterpene, a sesquiterpene, a diterpene, a flavonoid, a macrolide, a polyphenol, an anthocyanin, a saponin, a lignin, a coumarin, a glucoside, a quinine, an antimetabolite, an anthracycline, an antibiotic, a steroid, an inorganic compound, an organic compound, or a combination thereof. In an embodiment of the method, the second test sample includes a kinase inhibitor, a proteasome inhibitor, a protein inhibitor, an electron transport chain inhibitor, or a ribosomal inhibitor, or a combination thereof. In an embodiment of the method, the second test sample includes 2-(4-amino-1-isopropyl-1H-pyrazolo[3,4-d]pyrimidin-3-yl)-1H-indol-5-ol; 2-((4-(5-Ethylpyrimidin-4-yl)piperazin-1-yl)methyl)-5-(trifluoromethyl)-1H-benzo[d]imidazole; (2'Z,3'E)-6-Bromoindirubin-3'-oxime; (2R,6aS,12aS)-1,2,6,6a,12,12a-hexahydro-2-isopropenyl-8,9-dimethoxychromeno[3,4-b]furo(2,3-h)chromen-6-one; Benzyl N-[(2S)-4-methyl-1-[[(2S)-4-methyl-1-[[(2S)-4-methyl-1-oxopentan-2-yl] amino]-1-oxopentan-2-yl]amino]-1-oxopentan-2-yl] carbamate; or (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate; or a combination thereof. In an embodiment of the method, the first test sample includes the second test sample and at least one of a FDA approved drug, a natural product, an organic compound, an inorganic compound, or a combination thereof.

In an embodiment of the method, a decrease of from about 10% to about 80% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected. In an embodiment of the method, wherein a decrease of from about 10% to about 80% of at least one of a decrease in a number of nucleoli, a number of nucleoli-containing nuclei, and a number of nucleoli per nucleus relative to a control isolated cancer cell characterized by nucleolar hypertrophy is detected. In an embodiment of the method, an increase of from about 50% to about 400% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected. In an embodiment of the method, an increase of from about 150% to about 400% of at least one of an increase in a number of nucleoli, a number of nucleoli-containing nuclei, and a number of nucleoli per nucleus in the isolated cancer cell relative to a control isolated cancer cell is detected. In an embodiment of the method, the isolated cancer cells are selected from the group consisting of HCT-15, AGS, MDA-MB-231, MDA-MB-435, HeLa, HepG2, normal fibroblasts, and a sample from a cancer patient.

A method of reducing nucleolar hypertrophy in a human cancer cell is disclosed. In an embodiment, the method includes: contacting an isolated cancer cell characterized by nucleolar hypertrophy with a first test sample; and detecting a reduction of the nucleolar hypertrophy in the isolated cancer cell. In embodiment of the method, the step of detecting a reduction of the nucleolar hypertrophy in the isolated cancer cell includes: measuring at least one of a decrease in a number of nucleoli, a number of nucleoli-containing nuclei, and a number of nucleoli per nucleus in the isolated cancer cell relative to the isolated cancer cell characterized by nucleolar hypertrophy before contact with the first test sample. In an embodiment, the method includes detecting a reduction of the nucleolar hypertrophy in the isolated cancer cell including: measuring at least one of a decrease in a number of nucleoli, a number of nucleoli-containing nuclei, and a number of nucleoli per nucleus relative to a control isolated cancer cell characterized by nucleolar hypertrophy.

In an embodiment, the method further includes inducing nucleolar hypertrophy in an isolated cancer cell to form the isolated cancer cell characterized by nucleolar hypertrophy comprising: contacting an isolated cancer cell with a second test sample; and detecting an increase of nucleolar hypertrophy in the isolated cancer cell. In an embodiment, the method includes a step of detecting an increase of nucleolar hypertrophy in the isolated cancer cell including: measuring at least one of an increase in a number of nucleoli, a number of nucleoli-containing nuclei, and a number of nucleoli per nucleus in the isolated cancer cell relative to the isolated cancer cell before contact with second test sample. In an embodiment, the method includes a step of detecting an increase of nucleolar hypertrophy in the isolated cancer cell comprises: measuring at least one of an increase in a number of nucleoli, a number of nucleoli-containing nuclei, and a number of nucleoli per nucleus in the isolated cancer cell relative to a control isolated cancer cell.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown.

FIG. 9 is a high-throughput screening scheme of compounds on 384-well plate.

DETAILED DESCRIPTION

Figure 1:
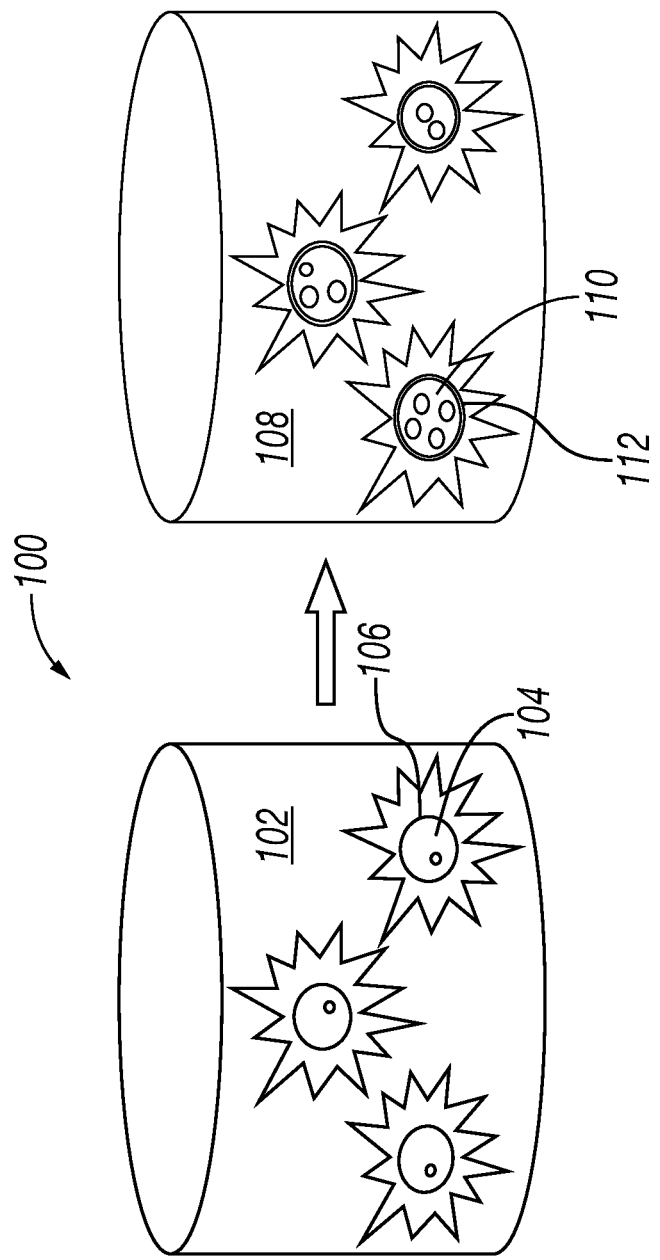
FIG. 1 is an artistic illustration of an embodiment of a method of screening a cancer cell by contacting the cancer cell with a substance to induce nucleolar hypertrophy in the cancer cell.

Unless otherwise noted, all measurements are in standard metric units.

Unless otherwise noted, all instances of the words "a," "an," or "the" can refer to one or more than one of the word that they modify.

Unless otherwise noted, the term "about" refers to ±10% of the non-percentage number that is described, and rounded to the nearest whole integer. For example, about 100 mm, would include 90 to 110 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 100 to about 200 mm would include from 90 to 220 mm.

As used herein, "rpL7a" refers to the ribosomal protein in humans that is encoded by the RPL7A gene.

As used herein, "GFP" refers to the green fluorescent protein that exhibits bright green fluorescence when exposed to light in the blue to ultraviolet range. In cell and molecular biology, the GFP gene frequently is utilized as a reporter of protein expression (synthesis).

As used herein, "antibody" refers to an immunoglobulin molecule having a specific amino acid sequence that gives each antibody the ability to adhere to and interact only or highly selectively with the antigen that induced its synthesis.

As used herein, "inducer" or "inducing agent" refers to a substance that causes, increases, generates or leads to nucleolar hypertrophy.

As used herein, "suppressor," "inhibitor," or "reducing agent" refers to a substance that inhibits or reduces nucleolar hypertrophy.

As used herein, the term "fraction" in reference to cells refers to proteins separated from the biological materials (cells).

As used herein, "nucleus" or "nuclei" refers to a membrane-enclosed organelle of a cell that contains genetic material.

As used herein, "nucleolus" or "nucleoli" refers to the largest structure in the nucleus. It is believe that the nucleolus primary serves as a site of ribosome assembly.

As used herein, "nucleolar hypertrophy," "nucleolus hypertrophy" or "nucleoli hypertrophy" refers to a nucleolar anomaly that manifests as an increase in the number of a number of nucleoli, a number of nucleoli-containing nuclei, a number of nucleoli per nucleus, or extended size of the nucleolus.

As used herein, "perinucleus" refers to a structure of the cell that is adjacent to the nucleus region and that provides protein translation that is distinct from that of the nucleus when cytoplasmic protein translation is suppressed. It is believed that this distinct protein translation causes nucleolar hypertrophy, which increases the chances of survival for cancer cells.

As used herein, "perinuclear wall" refers to filamentous structure surrounding the nucleus at certain distance forming a "cage" like structure that separates the perinucleus from the cytoplasm.

As used herein, "inner nuclear membrane" refers to the nuclear membrane that separates the nucleus from the perinucleus.

As used herein, "ribosome" or "polysome" refers to a complex molecular machine, found within all living cells, that serves as the site of biological protein synthesis (translation). Ribosomes link amino acids together in the order specified by messenger RNA (mRNA) molecules. Ribosomes consist of two major components: the small ribosomal subunit, which reads the RNA, and the large subunit, which joins amino acids to form a polypeptide chain. Each subunit is composed of one or more ribosomal RNA (rRNA) molecules and a variety of ribosomal proteins. The ribosomes and associated molecules are also known as the translational apparatus. A polyribosome (or polysome) is a complex of an mRNA molecule and two or more ribosomes that are formed during active translation.

As used herein, "mTOR" refers to mechanistic target of rapamycin, which is a protein kinase that phosphorylates Serine (Ser) or Threonine (Thr) amino acid residues of proteins.

As used herein, "kinase" refers to enzymes that phosphorylate Ser or Thr containing proteins.

As used herein, "eIF4" refers to eukaryotic initiation factor 4, the protein involved in the initiation phase of eukaryotic translation.

As used herein, "4E-BP1" refers to eukaryotic initiation factor 4 binding protein 1. It is believed that the interaction of this protein with eIF4E inhibits complex assembly and represses translation. Phosphorylation of this protein by mTOR releases it from eIF4 that initiates the protein translation.

As used herein, "eEF2k" refers to eukaryotic elongation factor 2 kinase, the enzyme that phosphorylates eEF-2 at Thr-56, which leads to inhibition of the elongation phase of protein synthesis.

As used herein, "p70S6K1" refers to ribosomal S6 protein kinase 1, the enzyme that phosphorylates ribosomal S6 protein.

As used herein, "rpS6" refers to a ribosomal protein of the small subunit.

As used herein, "multi-well plate" refers to a plates, including plastic plates, that contain varied amounts of wells (6, 12, 24, 48, 96, or 384) used to grow mammalian cells.

As used herein, "MTT" refers to the chemical compound 3-(4,5-dimethylthiazol-2-yl)-2,5-diphenytetrazolium bromide.

As used herein, "cytometer" refers to a device that measures the characteristics of cells, including the number of cells.

Unless otherwise noted, a "subject" as used herein can include a human, a dog, a cat, a rat, or any other mammal known to suffer from a cellular proliferative disorder, including cancer.

As used herein, an "anti-cancer compound" refers to any compound known or used to treat a cellular proliferative disorder, including cancer.

The present disclosure is based on science outside of the mainstream. As early as 1936, it was discovered that cancer cells in tissue have a nucleolus morphology that differs from non-cancer cells. Although there were no consistent differences in morphology, the nucleolus of cancer cells often appeared to be swollen with thicker structures than the non-cancer cells. Nucleolar hypertrophy was first observed more than 100 years ago, and it is a well-known historical hallmark of cancers that is used by pathologists to diagnose cancer. However, a lack of experimental approaches under laboratory conditions has prevented a conclusive understanding about its contribution to cancer cell survival. It is believed that the nucleolus is the site where ribosome biogenesis takes place. It is theorized that the changes to the nucleolar morphology were a part of a cellular defensive mechanism in response to micro-environmental harms, and might be triggered by one or more of the substances in chemotherapy. One explanation for the morphological change in a cancer cell's nucleolus could be that the nucleolus provides a layer of protection against conventional anticancer drugs. It has been observed that nucleolar hypertrophy correlates with perinuclear protein biosynthesis. The morphological alteration called "nucleolar hypertrophy" seems to reflect a defensive protein synthesis pathway at the perinuclear region in response to stress.

The present disclosure is based on the idea that the nucleolus does exist and that the nucleolus is a nuclear subdomain that serves as a site for ribosome biogenesis and ribosome subunit assembly. Nucleolar hypertrophy (NHT) can be thought of as a swelling of the nucleolus. This swelling can occur for a variety of reasons, and may be a basis for the morphological changes observed in cancer cells, especially those resistant to chemotherapy. The exact causes of nucleolar hypertrophy changes in cancer cells are still unclear. It is believed that when an anticancer drug slows or stops part of a cellular process, such as by inhibiting ribosomes, then the NHT may be linked to an increase of ribosome biogenesis, cell metabolic activity, cell proliferation rate, growth factors, oncogene and tumor suppressors proteins expression, cell doubling time, cell kinetics, neoplastic transformation, and stress. Therefore, it is believed that nucleolar hypertrophy may be linked to a cellular defense that plays a pivotal role in the survival and growth of drug resistant cancer cells.

A method of screening a cancer cell of a human subject for a nucleolar hypertrophy reducing agent is disclosed herein. Referring to FIG. 1, the method of screening a cancer cell includes contacting an isolated or purified cancer cell characterized by nucleolar hypertrophy with a first test sample or nucleolar hypertrophy reducing agent; and determining or measuring if the first test sample or nucleolar hypertrophy reducing agent reduces the nucleolar hypertrophy in the isolated cancer cell. In an embodiment, the method of screening a cancer cell includes contacting an isolated or purified cancer cell of the human subject with a second test sample or nucleolar hypertrophy inducing agent; and determining or measuring if the second test sample or nucleolar hypertrophy inducing agent induces or leads to nucleolar hypertrophy in the isolated cancer cell. The terms "first" and "second" when modifying "test sample" are an arbitrary naming convention and do not reflect the order of contacting the cancer cell.

The term "contacting" is not limited and can include any method of bringing a test sample into the presence of the cancer cell. Suitable methods for contacting a cancer cell with a test sample include adding, spraying, or dropping the test sample onto or near the cancer cell. The term "isolated" as used herein refers to a cell that is not in contact with surrounding tissue. The term "purified" refers to a cell that is not in contact with surrounding tissue or any other type of cell. Suitable isolated or purified cancer cells of a human subject include cells from a perpetual line of cells, including HCT-15, AGS, MDA-MB-231, MDA-MB-435, HeLa, and HepG2. The term "test sample" refers to one or more substances. The term "substance" refers to one or more compounds, molecules, or a combination thereof.

In an embodiment of the method, the first test sample includes a nucleolar hypertrophy reducing agent. In an embodiment, the first test sample or nucleolar hypertrophy reducing agent can include an FDA approved drug, a natural product, an alkaloid, a monoterpene, a sesquiterpene, a diterpene, a flavonoid, a macrolide, a polyphenol, an anthocyanin, a saponin, a lignin, a coumarin, a glucoside, a quinine, an antimetabolite, an anthracycline, an antibiotic, a steroid, an inorganic compound, an organic compound, or a combination thereof.

In an embodiment of the method, the second test sample includes a nucleolar hypertrophy inducing agent. In an embodiment, the second test sample or nucleolar hypertrophy inducing agent can include a kinase inhibitor, a proteasome inhibitor, a protein inhibitor, an electron transport chain inhibitor, or a ribosomal inhibitor, or a combination thereof. In an embodiment, the second test sample or nucleolar hypertrophy inducing agent can include "pp242" (2-(4-amino-1-isopropyl-1H-pyrazolo[3,4-d]pyrimidin-3-yl)-1H-indol-5-ol); "PF-4708671" (2-((4-(5-Ethylpyrimidin-4-yl)piperazin-1-yl)methyl)-5-(trifluoromethyl)-1H-benzo[d]imidazole); "Bio" (2'Z,3'E)-6-Bromoindirubin-3'-oxime; "rotenone" (2R,6aS,12a5)-1,2,6,6a,12,12a-hexahydro-2-isopropenyl-8,9-dimethoxychromeno[3,4-b]furo(2,3-h)chromen-6-one; "MG132" Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate; and/or "Geldanamycin" (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate; or a combination thereof.

It is understood that many targeted cancer therapies pursue a single gene alteration which cancer cells can bypass. In an embodiment, the present disclosure provides a high throughput method for identifying substances that suppress or reduce the perinuclear mechanism of cancer cell survival. In an embodiment, the method comprises (a) contacting a cancer cell with an inhibitor or a nucleolar hypertrophy reducing agent; and (b) determining or measuring the response of one or more cancer cells to the nucleolar hypertrophy reducing agent. In an embodiment of the method, the nucleolar hypertrophy of the cancer cells was induced, caused, or set in motion by a nucleolar hypertrophy inducing agent. In embodiment of the method, the cancer cell response is determined by a method which includes counting a number of nucleoli, a number of nucleoli-containing nuclei, and/or a number of nucleoli per nucleus in the cancer cell. In an embodiment of the method, the cancer cell response is measured or compared relative to a control or the cancer cell before contact with the first or second test sample. In an embodiment of the method, determining if the first test sample reduces the nucleolar hypertrophy in the isolated cancer cell and/or determining if the second test sample induces nucleolar hypertrophy in the isolated cancer cell, includes expressing a ribosomal protein, including expressing rpL7a. In an embodiment, the method includes labeling the ribosomal protein with a fluorescent molecule. In an embodiment, the fluorescent molecule can include GFP or Alexa-488, 594 or any other fluorescent molecule from Alexa Fluor®. In an embodiment the ribosomal protein is labeled by forming an antibody-conjugate attachment directly or indirectly with the ribosomal protein. In an embodiment, Nuclear hypertrophy can be detected also by the staining methods such as: propidium iodide, SYBR® Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine), hematoxylin, eosin and other staining techniques.

One benefit of the present method can be an increases in the efficiency of a cancer treatment due to the reduction of cancer cell survival ability. It is believed that a common mechanism of cancer cell survival is located in the perinuclear region of the cell nucleus, where the translation of the nuclear proteins, particularly ribosomal proteins, takes place. It is believed that the quantity of the perinuclear ribosomes and polysomes can be correlated with the rate of cell proliferation. Nucleolar hypertrophy may reflect the increase of the perinuclear protein synthesis at cellular stress. The method disclosed herein treats cancer cells in a state of hypertrophy with a nucleolar hypertrophy reducing agent to reduce the nucleolar hypertrophy in the cancer cell by reducing or suppressing the rate of perinuclear protein synthesis.

Figure 2:
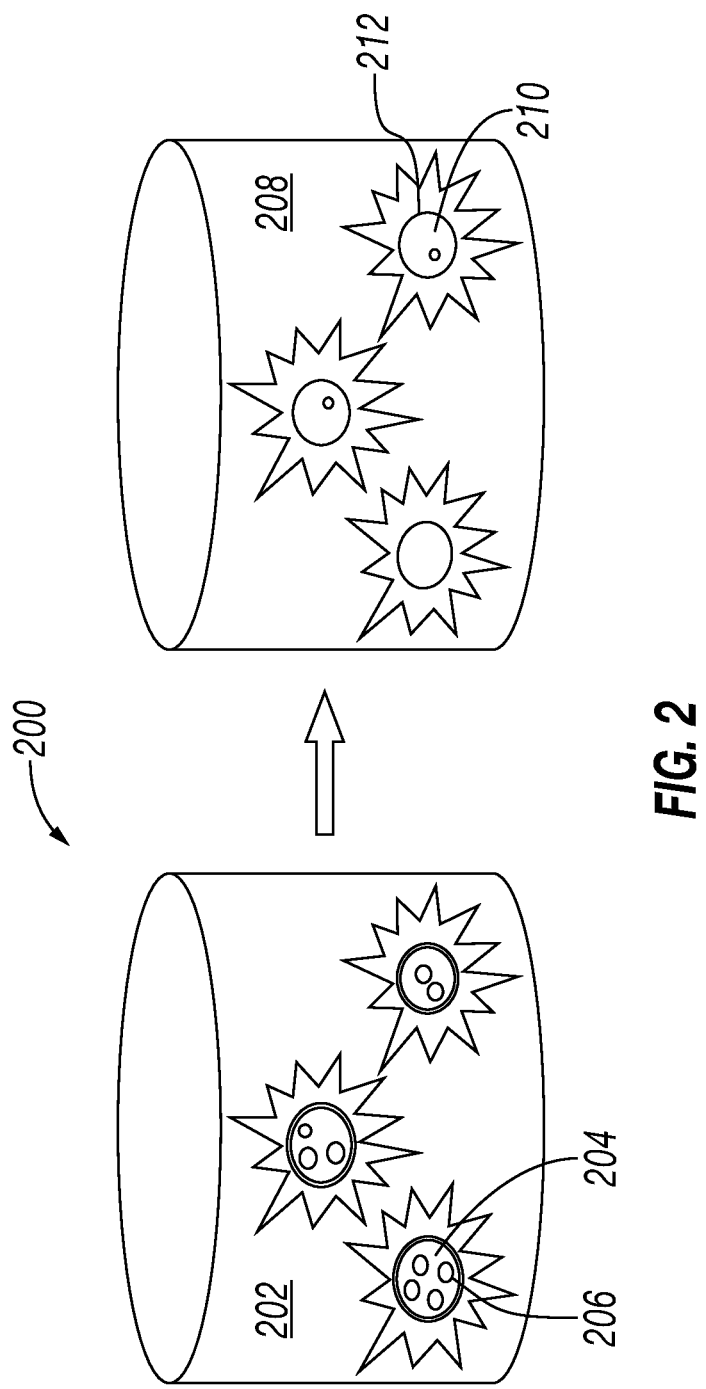
FIG. 2 is an artistic illustration of an embodiment of a method of screening a cancer cell characterized by nucleolar hypertrophy with a substance to reduce the nucleolar hypertrophy in the cancer cell.

Referring to FIG. 2, in an embodiment of the method, determining if a first test sample or nucleolar reducing agent reduces nucleolar hypertrophy in isolated cancer cell characterized by nucleolar hypertrophy (202), includes measuring a reduction in the number of nucleoli, a number of nucleoli-containing nuclei, or a number of nucleoli (204, 210) per nucleus (206, 212) in the cancer cell, or a combination thereof to provide an isolated cancer cell (208) characterized by no or reduced nucleolar hypertrophy. In an embodiment, this measurement can be performed relative to a control or the cancer cells prior to contact with the test sample. In an embodiment of the method, the method can identify or screen for a nucleolar hypertrophy reducing agent. In an embodiment, the nucleolar hypertrophy reducing agent can be coupled with any compatible cancer treatment to improve the efficacy of that treatment by reducing or suppressing the defensive mechanism of the cell.

Referring to FIG. 1, in an embodiment of the method, determining if a second test sample or nucleolar inducing agent induces nucleolar hypertrophy in an isolated cancer cell (102) to provide an isolated cancer cell characterized by nucleolar hypertrophy (108), includes measuring an increase in the number of nucleoli, a number of nucleoli-containing nuclei, or a number of nucleoli (104, 110) per nucleus (106, 112) in the cancer cell, or a combination thereof to provide an isolated cancer cell (108) characterized by nucleolar hypertrophy.

Figure 11:
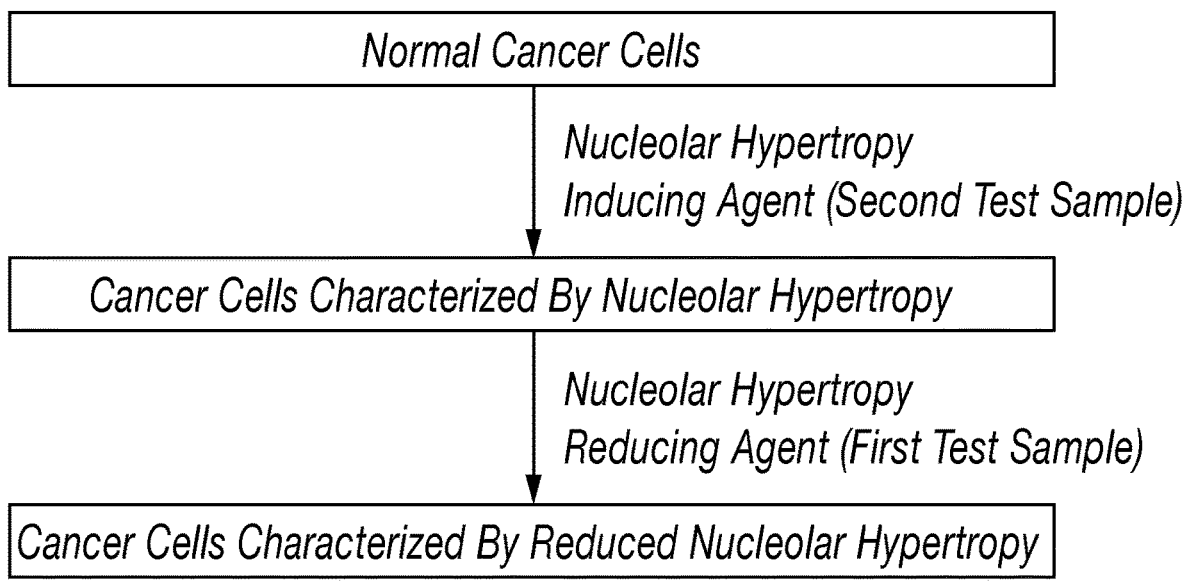
FIG. 11 is a flow diagram of an embodiment of a method of screening test samples.

Referring to FIG. 11, in an embodiment of the method, isolated cancer cells are contacted with a second test sample or nucleolar hypertrophy inducing agent to induce or provide isolated cancer cells characterized by nucleolar hypertrophy, and then the isolated cancer cells characterized by nucleolar hypertrophy are contacted by a first test sample or nucleolar hypertrophy reducing agent to reduce the nucleolar hypertrophy or to provide cancer cells characterized by no or reduced nucleolar hypertrophy.

In an embodiment, the method includes growing a cancer or normal cells on multi-well plates and adding a nucleolar hypertrophy inducing agent to the cancer or normal cells. In an embodiment, the method includes the detection of a nucleoli signal by ribosomal protein L7a localization with the corresponding first and secondary antibodies that specifically bind to the protein and first antibody. In an embodiment, the identification of the signal by the Alexa-488 (or other conjugates) is highly selective and can be scanned or measured by a cytometer. In an embodiment, the data from the cytometer can be analyzed with an algorithm developed in MatLab (Mathworks).

In an embodiment, the method includes screening anticancer drugs that suppress a cancer cell survival mechanism of solid tumors that display nucleolar hypertrophy, where the nucleolar hypertrophy reflects an increase of the perinuclear protein synthesis. Accordingly, the following discussion will describe some of the characteristics of these cancer cells, regulation of the protein synthesis, and methods of detection of nucleolar hypertrophy and/or perinuclear protein synthesis.

In an embodiment, the cells may be cultured by techniques well known to those skilled in the art. In an embodiment, the cells are cultivated in a nutrient medium that supports cell viability and growth. In an embodiment, while the medium may vary, depending upon the particular cells employed, suitable media include Dulbecco's modified Eagle's medium ("DMEM") or Roswell Park Memorial Institute medium (RPMI-1640) supplemented with 10% fetal bovine serum. In an embodiment of the method, culture plates can be advantageously maintained in humidified incubation chambers at 37° C. in an atmosphere containing 5% carbon dioxide.

In an embodiment, the cell-containing media can be added to the wells of a microtiter plate. In an embodiment, a preferred format for carrying out the screening method utilizes a 384 microtiter plate. In an embodiment, each well can contain less than about 50 microliters of culture medium. In an embodiment, about 4000 cells can be seeded in one well. In an embodiment, the cells can be seeded using a multichannel pipette.

In an embodiment, once plated in the wells, the cells can be cultivated to a desired cell density, which is about 75% confluent condition. In an embodiment, when the cell growth has reached the desired density, the compounds to be tested or test samples can be added to the microtiter plate wells. In an embodiment, each compound being tested can be added to a plurality of wells at different concentrations.

In an embodiment, the compound can be added in dilutions that include a useful dose-response curve. In an embodiment, if concentrations are selected appropriately, the results of the method can be expressed as the concentration of the compound that is effective in inhibiting or promoting nucleolar hypertrophy.

In an embodiment, blank wells, which contain cells and media, but do not contain a test compound, can be included as controls. Positive controls, i.e., compounds which are known to promote nucleolar hypertrophy, can also be included. In an embodiment, a wide variety of different types of potential anticancer agents may be tested as a test sample. For example, chemical agents, natural agents, such as extracts of plants, bacteria and fungi, and many other types of agents may be tested as a test sample.

In an embodiment, once the desired cell density has been reached, the culture medium can be removed from each well and replaced with a culture medium containing the test sample or test compound. In an embodiment, the cultivation typically spans several hours to a maximum of 24 hrs. In an embodiment, the method permits the use of the test sample or test compound concentrations in the micromolar range and below. In an embodiment, the concentrations generally range from about 10 nanomolar to about 1 millimolar. In an embodiment, concentrations can be adjusted after initial results to obtain a useable dose-response curve.

In an embodiment, after the cells have been cultivated in the presence of test compounds or test samples for a time sufficient for nucleoli alteration, the culture medium can be removed. In an embodiment, cells can be fixed with 4% paraformaldehyde (PFA) for 15 min at room temperature, and washed three times with the phosphate buffered saline (PBS) for 5 min each.

In an embodiment, cells can be permeabilized with permeabilization buffer containing 1% Triton-X100 for 45 minutes, then cells can be rinsed three times in PBS for 5 min each, cells can be blocked with 5% goat serum for 1 hour, and incubated with anti-rpL7a antibody overnight at 1:500 dilution in antibody dilution buffer at 4° C.

In an embodiment, the next day, the cells can be washed tree times with the PBS for 5 min each and incubated with Alexa 488-conjugated secondary antibody for 2-3 hours at room temperature in the dark, diluted 1:500 in antibody dilution buffer. In an embodiment, a secondary antibody can be directed against the species of the first antibody and can be different from the Alexa-Flour conjugate. In an embodiment, cells are rinsed in 1% goat serum containing PBS twice, away from the light and nuclei are stained with 300 ng/ml DAPI (4,6-Diamidino-2-phenylindole, dihydrochloride) away from the light. In an embodiment, cells can be rinsed three times in PBS for 5 min each and kept in the dark until scanning with the cytometer.

In an embodiment, cells can be imaged on an IC200 high-throughput image cytometer (VALA Sciences) using a Plan-Apochromat 40× objective. In an embodiment, a single plane can be acquired in the DAPI channel, and a z-stack series (10 μm in 1-μm increments) is acquired in the GFP channel. In an embodiment, image analysis can be performed using a custom-made algorithm developed by MatLab. In an embodiment, two fields-of-view (FOV) per well were analyzed (average of 46 cells per FOV). In an embodiment, each FOV, DAPI-labeled nuclei was segmented using a watershed transform strategy. In an embodiment, for nucleolus segmentation, the best focused GFP-labeled nucleoli plane can be selected, and objects are identified by first performing a morphological top-hat filtering, followed by computing the regional maxima of the H-maxima transform.

First Set of Example Embodiments

1. A method for screening a cancer cell of a human subject for a nucleolar hypertrophy reducing agent comprising:

contacting an isolated cancer cell characterized by nucleolar hypertrophy with a first test sample; and determining if the first test sample reduces the nucleolar hypertrophy in the isolated cancer cell.

2. The method of embodiment 1, wherein determining if the first test sample reduces the nucleolar hypertrophy in the isolated cancer cell comprises:

measuring at least one of a decrease in a number of nucleoli, a number of nucleoli-containing nuclei, and a number of nucleoli per nucleus in the isolated cancer cell relative to the isolated cancer cell characterized by nucleolar hypertrophy before contact with the first test sample.

3. The method according to any one of embodiments 1-2, wherein determining if the first test sample reduces the nucleolar hypertrophy in the isolated cancer cell comprises:

measuring at least one of a decrease in a number of nucleoli, a number of nucleoli-containing nuclei, and a number of nucleoli per nucleus relative to a control isolated cancer cell characterized by nucleolar hypertrophy.

4. The method of according to any one of embodiments 1-3, further comprising:

screening the cancer cell of the human subject for a nucleolar hypertrophy inducing agent comprising:

contacting the isolated cancer cell with a second test sample; and determining if the second test sample induces nucleolar hypertrophy in the isolated cancer cell.

5. The method of embodiment 4, wherein determining if the second test sample induces nucleolar hypertrophy in the isolated cancer cell comprises:

measuring at least one of an increase in a number of nucleoli, a number of nucleoli-containing nuclei, and a number of nucleoli per nucleus in the isolated cancer cell relative to the isolated cancer cell before contact with second test sample.

6. The method according to any one of embodiments 4-5, wherein determining if the second test sample induces nucleolar hypertrophy in the isolated cancer cell comprises:

measuring at least one of an increase in a number of nucleoli, a number of nucleoli-containing nuclei, and a number of nucleoli per nucleus in the isolated cancer cell relative to a control isolated cancer cell.

7. The method according to any one of embodiments 1-6, where the first test sample comprises an FDA approved drug, a natural product, an alkaloid, a monoterpene, a sesquiterpene, a diterpene, a flavonoid, a macrolide, a polyphenol, an anthocyanin, a saponin, a lignin, a coumarin, a glucoside, a quinine, an antimetabolite, an anthracycline, an antibiotic, a steroid, an inorganic compound, an organic compound, or a combination thereof.

8. The method according to any one of embodiments 4-7, wherein the second test sample includes a kinase inhibitor, a proteasome inhibitor, a protein inhibitor, an electron transport chain inhibitor, or a ribosomal inhibitor, or a combination thereof.

9. The method according to any one of embodiments 4-8, wherein the second test sample includes 2-(4-amino-1-isopropyl-1H-pyrazolo[3,4-d]pyrimidin-3-yl)-1H-indol-5-ol; 2-((4-(5-Ethylpyrimidin-4-yl)piperazin-1-yl)methyl)-5-(trifluoromethyl)-1H-benzo[d]imidazole; (2'Z,3'E)-6-Bromoindirubin-3'-oxime; (2R,6aS,12aS)-1,2,6,6a,12,12a-hexahydro-2-isopropenyl-8,9-dimethoxychromeno[3,4-b]furo(2,3-h)chromen-6-one; Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl] carbamate; or (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate; or a combination thereof.

10. The method according to any one of embodiments 1-9, wherein the first test sample includes the second test sample and at least one of a FDA approved drug, a natural product, an organic compound, an inorganic compound or a combination thereof.

11. The method according to any one of embodiments 1-10, wherein a decrease of from about 10% to about 80% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected.

12. The method according to any one of embodiments 1-11, wherein a decrease of from about 10% to about 80% of at least one of a decrease in a number of nucleoli, a number of nucleoli-containing nuclei, and a number of nucleoli per nucleus relative to a control isolated cancer cell characterized by nucleolar hypertrophy is detected.

13. The method according to any one of embodiments 4-12, wherein an increase of from about 50% to about 400% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected.

14. The method according to any one of embodiments 4-13, wherein an increase of from about 150% to about 400% of at least one of an increase in a number of nucleoli, a number of nucleoli-containing nuclei, and a number of nucleoli per nucleus in the isolated cancer cell relative to a control isolated cancer cell is detected.

15. The method according to any one of embodiments 1-14, wherein the isolated cancer cells are selected from the group consisting of HCT-15, AGS, MDA-MB-231, MDA-MB-435, HeLa, HepG2, normal fibroblasts, and a sample from a cancer patient or any other known cell lines.

16. A method of reducing nucleolar hypertrophy in a human cancer cell comprising: contacting an isolated cancer cell characterized by nucleolar hypertrophy with a first test sample; and detecting a reduction of the nucleolar hypertrophy in the isolated cancer cell.

17. The method of embodiment 16, wherein detecting a reduction of the nucleolar hypertrophy in the isolated cancer cell comprises:

measuring at least one of a decrease in a number of nucleoli, a number of nucleoli-containing nuclei, and a number of nucleoli per nucleus in the isolated cancer cell relative to the isolated cancer cell characterized by nucleolar hypertrophy before contact with the first test sample.

18. The method according to any one of embodiments 16-17, wherein detecting a reduction of the nucleolar hypertrophy in the isolated cancer cell comprises:

measuring at least one of a decrease in a number of nucleoli, a number of nucleoli-containing nuclei, and a number of nucleoli per nucleus relative to a control isolated cancer cell characterized by nucleolar hypertrophy.

19. The method according to any one of embodiments 16-18, further comprises:

inducing nucleolar hypertrophy in an isolated cancer cell to form the isolated cancer cell characterized by nucleolar hypertrophy comprising:

contacting an isolated cancer cell with a second test sample; and detecting an increase of nucleolar hypertrophy in the isolated cancer cell.

20. The method according to any one of embodiments 16-19, wherein detecting an increase of nucleolar hypertrophy in the isolated cancer cell comprises:

measuring at least one of an increase in a number of nucleoli, a number of nucleoli-containing nuclei, and a number of nucleoli per nucleus in the isolated cancer cell relative to the isolated cancer cell before contact with second test sample.

21. The method according to any one of embodiments 16-20, wherein detecting an increase of nucleolar hypertrophy in the isolated cancer cell comprises:

measuring at least one of an increase in a number of nucleoli, a number of nucleoli-containing nuclei, and a number of nucleoli per nucleus in the isolated cancer cell relative to a control isolated cancer cell.

A Second Set of Example Embodiments

1. A method for screening a cancer cell of a subject for a nucleolar hypertrophy reducing agent comprising:

contacting an isolated cancer cell characterized by induced nucleolar hypertrophy with a test sample; and determining if the test sample reduces the induced nucleolar hypertrophy in the isolated cancer cell.

2. The method of embodiment 1, wherein determining if the test sample reduces the induced nucleolar hypertrophy in the isolated cancer cell comprises:

measuring at least one of a decrease in a number of nucleoli, a number of nucleoli-containing nuclei, and a number of nucleoli per nucleus in the isolated cancer cell relative to the isolated cancer cell characterized by induced nucleolar hypertrophy before contact with the test sample.

3. The method according to any one of embodiments 1-2, wherein determining if the test sample reduces the induced nucleolar hypertrophy in the isolated cancer cell comprises:

measuring at least one of a decrease in a number of nucleoli, a number of nucleoli-containing nuclei, and a number of nucleoli per nucleus relative to a control isolated cancer cell characterized by induced nucleolar hypertrophy.

4. The method according to any one of embodiments 1-3, further comprising:

screening the cancer cell of the subject for a nucleolar hypertrophy inducing agent comprising:

contacting the isolated cancer cell with an anti-cancer compound; and determining if the anti-cancer compound induces nucleolar hypertrophy in the isolated cancer cell.

5. The method of embodiment 4, wherein determining if the anti-cancer compound induces nucleolar hypertrophy in the isolated cancer cell comprises:

measuring at least one of an increase in a number of nucleoli, a number of nucleoli-containing nuclei, and a number of nucleoli per nucleus in the isolated cancer cell relative to the isolated cancer cell before contact with the anti-cancer compound.

6. The method according to any one of embodiments 4-5, wherein determining if the anti-cancer compound induces nucleolar hypertrophy in the isolated cancer cell comprises:

measuring at least one of an increase in a number of nucleoli, a number of nucleoli-containing nuclei, and a number of nucleoli per nucleus in the isolated cancer cell relative to a control isolated cancer cell.

7. The method according to any one of embodiments 1-6, where the test sample comprises an FDA approved drug, a natural product, an alkaloid, a monoterpene, a sesquiterpene, a diterpene, a flavonoid, a macrolide, a polyphenol, an anthocyanin, a saponin, a lignin, a coumarin, a glucoside, a quinine, an antimetabolite, an anthracycline, an antibiotic, a steroid, an inorganic compound, an organic compound, or a combination thereof.

8. The method according to any one of embodiments 4-7, wherein the anti-cancer compound includes a kinase inhibitor, a proteasome inhibitor, a protein inhibitor, an electron transport chain inhibitor, or a ribosomal inhibitor, or a combination thereof 9. The method according to any one of embodiments 4-8, wherein the anti-cancer compound includes 2-(4-amino-1-isopropyl-1H-pyrazolo[3,4-d]pyrimidin-3-yl)-1H-indol-5-ol; 2-((4-(5-Ethylpyrimidin-4-yl)piperazin-1-yl)methyl)-5-(trifluoromethyl)-1H-benzo[d]imidazole; (2'Z,3'E)-6-Bromoindirubin-3'-oxime; (2R,6aS,12aS)-1,2,6,6a,12,12a-hexahydro-2-isopropenyl-8,9-dimethoxychromeno[3,4-b]furo(2,3-h)chromen-6-one; benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate; or (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate; or a combination thereof.

10. The method according to any one of embodiments 1-9, wherein the test sample includes the anti-cancer compound and at least one of a FDA approved drug, a natural product, an organic compound, an inorganic compound or a combination thereof.

11. The method according to any one of embodiments 1-10, wherein a decrease of from about 10% to about 80% of at least one of a number of nucleoli, a number of nucleoli-containing nuclei, and a number of nucleoli per nucleus in the isolated cancer cell relative to the isolated cancer cell characterized by induced nucleolar hypertrophy before contact with the test sample is detected.

12. The method according to any one of embodiments 1-11, wherein a decrease of from about 10% to about 80% of at least one of a decrease in a number of nucleoli, a number of nucleoli-containing nuclei, and a number of nucleoli per nucleus relative to a control isolated cancer cell characterized by induced nucleolar hypertrophy is detected.

13. The method according to any one of embodiments 4-12, wherein an increase of from about 50% to about 400% of at least one of a number of nucleoli, a number of nucleoli-containing nuclei, and a number of nucleoli per nucleus in the isolated cancer cell relative to the isolated cancer cell characterized by induced nucleolar hypertrophy before contact with the test sample is detected.

14. The method according to any one of embodiments 4-13, wherein an increase of from about 150% to about 400% of at least one of an increase in a number of nucleoli, a number of nucleoli-containing nuclei, and a number of nucleoli per nucleus in the isolated cancer cell relative to a control isolated cancer cell is detected.

15. The method according to any one of embodiments 1-14, wherein the isolated cancer cells are selected from the group consisting of HCT-15, AGS, MDA-MB-231, MDA-MB-435, HeLa, HepG2, normal fibroblasts, and a sample from a cancer patient or any other known cell lines.

16. A method of reducing nucleolar hypertrophy in a cancer cell comprising:

contacting an isolated cancer cell characterized by induced nucleolar hypertrophy with a test sample; and detecting a reduction of the induced nucleolar hypertrophy in the isolated cancer cell.

17. The method of embodiment 16, wherein detecting a reduction of the induced nucleolar hypertrophy in the isolated cancer cell comprises:

measuring at least one of a decrease in a number of nucleoli, a number of nucleoli-containing nuclei, and a number of nucleoli per nucleus in the isolated cancer cell relative to the isolated cancer cell characterized by induced nucleolar hypertrophy before contact with the test sample.

18. The method according to any one of embodiments 16-17, wherein detecting a reduction of the induced nucleolar hypertrophy in the isolated cancer cell comprises:

measuring at least one of a decrease in a number of nucleoli, a number of nucleoli-containing nuclei, and a number of nucleoli per nucleus relative to a control isolated cancer cell characterized by induced nucleolar hypertrophy.

19. The method according to any one of embodiments 16-18, further comprises:

inducing nucleolar hypertrophy in an isolated cancer cell to form the isolated cancer cell characterized by induced nucleolar hypertrophy comprising:

contacting an isolated cancer cell with an anti-cancer compound; and detecting an increase of nucleolar hypertrophy in the isolated cancer cell.

20. The method according to any one of embodiments 16-19, wherein detecting an increase of nucleolar hypertrophy in the isolated cancer cell comprises:

measuring at least one of an increase in a number of nucleoli, a number of nucleoli-containing nuclei, and a number of nucleoli per nucleus in the isolated cancer cell relative to the isolated cancer cell before contact with the anti-cancer compound.

21. The method according to any one of embodiments 16-20, wherein detecting an increase of nucleolar hypertrophy in the isolated cancer cell comprises:

measuring at least one of an increase in a number of nucleoli, a number of nucleoli-containing nuclei, and a number of nucleoli per nucleus in the isolated cancer cell relative to a control isolated cancer cell.

EXPERIMENTAL

Solutions, buffers and reagents:
1. Preparing PBS from 10×PBS: Add 100 ml 10×PBS to 900 ml water, adjust pH to 8.0.
2. To prepare 4% paraformaldehyde (PFA) fixing solution from 16% PFA methanol free paraformaldehyde, mix 1 ml PFA and 3 ml PBS. Use fresh and store opened vials at 4° C. in dark.
3. Permeabilization buffer contains 1% Triton X-100 in PBS. To prepare, dilute 1 ml Triton X-100 in 99 ml PBS.
4. Blocking Buffer contains 5% normal serum in PBS with 0.3% Triton™ X-100. To prepare 10 ml, add 0.5 ml normal serum from the same species as the secondary antibody and while stirring, add 30 µl Triton™ X-100.
5. Antibody Dilution Buffer contains 1% BSA (bovine serum albumin) in PBS with 0.3% Triton X-100. To prepare 10 ml, add 30 µl Triton™ X-100 to 10 ml PBS. Mix well then add 0.1 g BSA, mix.

General Preparation

Into each well of a 384-well plate (Greiner), 4,000 cells (HCT-15 or others as indicated above) are seeded and incubated overnight according to FIG. 9. The next day, wells (A 1,2 & B 1,2) are marked as control and remain untreated. The wells (I1,2 & J1,2) are treated with 500 mM pp242 or other nucleolar hypertrophy inducing agent for 1-3 hours. The wells (A3-A24; B3-B24; C1-C24; D1-D24; E1-E24; F1-F24; G1-G24; H1-H24) are treated with the testing compounds in four repeats. The wells (I3-I24; J3-J24; K1-K24; L1-L24; M1-M24; N1-N24; O1-O24; P1-P24) are treated with the testing compounds and pp242 or other nucleolar hypertrophy inducing agent for 1-3 hours, in four repeats. Cells are fixed with 4% PFA for 30 minutes, permeabilized with 1% Triton-X100 for 1 hour, blocked with goat serum for 1 hour, and incubated with anti-rpL7a antibody overnight, followed by Alexa 488-conjugated secondary antibody for 1 hour.

Nuclei are stained with DAPI. Cells are imaged on an IC200 high-throughput image cytometer (VALA Sciences) using a Plan-Apochromat 40× objective. A single plane is acquired in the DAPI channel, and a z-stack series (10 µm in 1-µm increments) is acquired in the GFP channel. Image analysis is performed using a custom-made algorithm developed in MatLab. The algorithm was commercially developed by the company Mathworks in MA. Two fields-of-view (FOV) per well are analyzed (average of 46 cells per FOV). For each FOV, DAPI-labeled nuclei were segmented using a watershed transform strategy. For nucleolus segmentation, the best focused GFP-labeled nucleoli plane needs to be selected, and objects are identified by first performing a morphological top-hat filtering, followed by computing the regional maxima of the H-maxima transform. From these images, the following features needs to be quantified: a number of nucleoli, a number of nucleoli-containing nuclei, and a number of nucleoli per nucleus, percentage of nuclei-containing nucleoli, and average number of nucleoli per nucleus.

Example 1

The common trait of almost all solid tumor cancer cells is the generation of nucleolar anomaly which implies an extensive ribosome biogenesis. The mechanism of nucleolar hypertrophy was not known since it was difficult to manipulate or quantify the nucleolar abnormality under the conditions of laboratory experiments.

To detect perinuclear protein synthesis and nucleolar hypertrophy at stress, the green fluorescent protein (GFP) tagged ribosomal protein L7a (GFP-L7a) was expressed in HCT-15 cells. Ribosomal protein L7a (rpL7a) contains a domain II (residues 52-100) that directs the nucleolar accumulation. To further assess protein biosynthesis in the perinuclear area and ribosome biogenesis, several chemical agents were tested on cellular growth and survival. The results are shown in FIG. 8.

Figure 7:
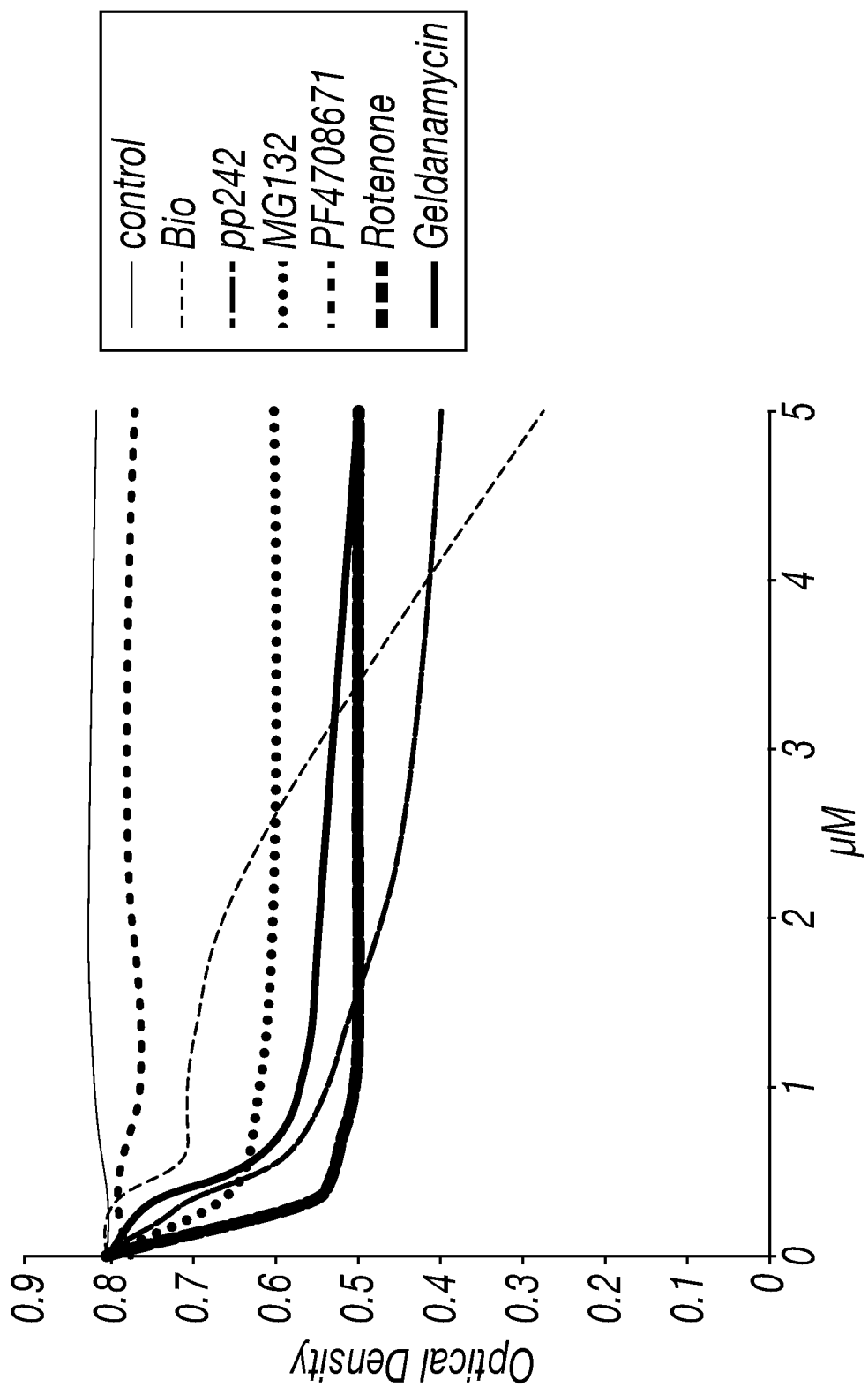
FIG. 7 is a graph of the cell survival assay using the MTT to assess cell metabolic activity.

All the tested compounds were dissolved in dimethylsulfoxide (DMSO). Compounds that inhibit protein biosynthesis (pp242 and PF4708671), protein degradation (MG132 and Geldanamycin), and mitochondrial function (Rotenone) showed no toxicity at the applied concentrations. However, except for PF4708671, they inhibited cellular proliferation during prolonged 24-hour treatments. Bio, a GSK-3 inhibitor that inhibits numerous protein kinases, was more toxic than the other compounds. The results of the toxicity study are shown in FIG. 7. pp242 inhibited both mTOR complexes and impacts numerous processes in the cell, including autophagy activation, which invokes the cellular stress response. The effects of other compounds suggest that they also act to induce or trigger cell survival mechanisms too.

Cell Culture

The human colorectal adenocarcinoma cell lines: HCT-15 was purchased from ATCC. Cultures of cells maintained in DMEM/F12 medium containing 10% FBS and antibiotics, at 37° C. with 5% $CO_2$. For cell treatments, cells were grown at 80% confluence in complete medium.

Example 2

Figure 10:
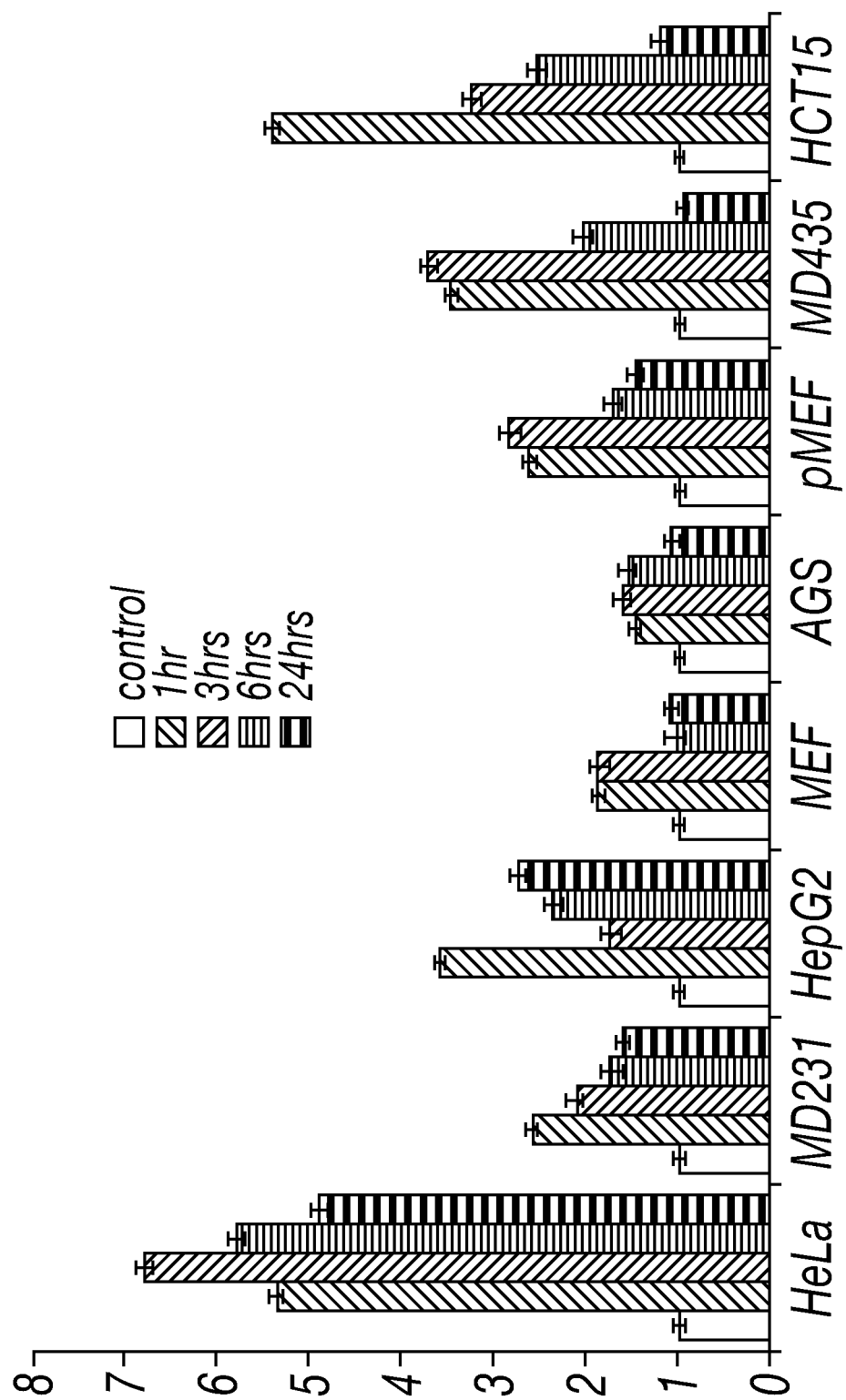
FIG. 10 is a bar graph of a high throughput assessment of the effect of pp242 on nucleolar hypertrophy on multiple cell lines.

After confirmation that all tested compounds are useful agents for the induction of perinuclear protein synthesis and nucleolar hypertrophy, pp242 was selected as a primary compound for high-throughput assessment of its effect on a broad range of cell lines. Cells were treated for time periods 1 hour, 3 hours, 6 hours, and 24 hours and the number of nucleoli per cell nucleus was measured (FIG. 10).

The following data was generated:

HeLa Cells

A 5.4 fold increase at 1st hr; 6.8 fold increase at 3rd hrs, 5.8 fold increase at 6th hrs, and 4.8 fold increase in 24th hrs was observed in HeLa cells, which supports the notion that nucleolar hypertrophy is reversible.

MDA-MB-231

A 2.5 fold increase at 1st hr; 2.1 fold increase at 3rd hrs, 1.8 fold increase at 6th hrs, and 1.5 fold increase in 24th hrs was observed in MDA-MB-231 cells, which supports the notion that nucleolar hypertrophy is reversible.

HepG2 Cells

A 3.5 fold increase at 1st hr; 1.8 fold increase at 3rd hrs, 2.5 fold increase at 6th hrs, and 2.8 fold increase in 24th hrs was observed in HepG2 cells. HepG2 cells are liver cancer cells with the high metabolism that can also produce more toxic products. The fluctuation of nucleoli indicates that the nucleolar hypertrophy is flexible.

Normal Mouse Embryonal Fibroblast Cells

A 1.8 fold increase at 1st and 3rd hrs, and reversion of nucleoli hypertrophy at 6th hrs, and 24th hrs was observed in normal fibroblast cells which indicate that the nucleolar hypertrophy is reversible.

AGS Cells

An about 1.5 fold increase at 1st, 3rd, and 6th hrs and reversion of nucleoli hypertrophy at 24th hrs was observed in AGS cells which indicate that the nucleolar hypertrophy is reversible.

Immortalized Mouse Embryonal Fibroblast Cells

An about 2.7 fold increase at 1st, 3rd hrs and about 1.5 fold increase at 6th and at 24th hrs was observed in immortalized normal fibroblast cells which indicate that the nucleolar hypertrophy is reversible.

MDA-MB-435

An about 3.5 fold increase at 1st, 3rd, and 2 fold increase at 6th hrs and complete reversion of nucleoli hypertrophy at 24th hrs was observed in MDA-MB-435 cells which indicate that the nucleolar hypertrophy is reversible.

HCT-15 Cells

A 5 fold increase at 1st hr; 3.5 fold increase at 3rd hrs, 2.5 fold increase at 6th hrs, and reversion in 24th hrs was observed in HCT-15 cells which indicate that the nucleolar hypertrophy is reversible.

Cell Culture

The cell lines: AGS, HeLa, MDA-MB-435, MDA-MB-231, and HepG2 cells were purchased from ATCC and grown in 384 well plates. Cells cultured in DMEM/F12 medium containing 10% FBS and antibiotics, at 37° C. with 5% $CO_2$. Cells were grown in complete medium and treated with the 500 nM of pp242.

Experimental Results and Data

Figure 3B:
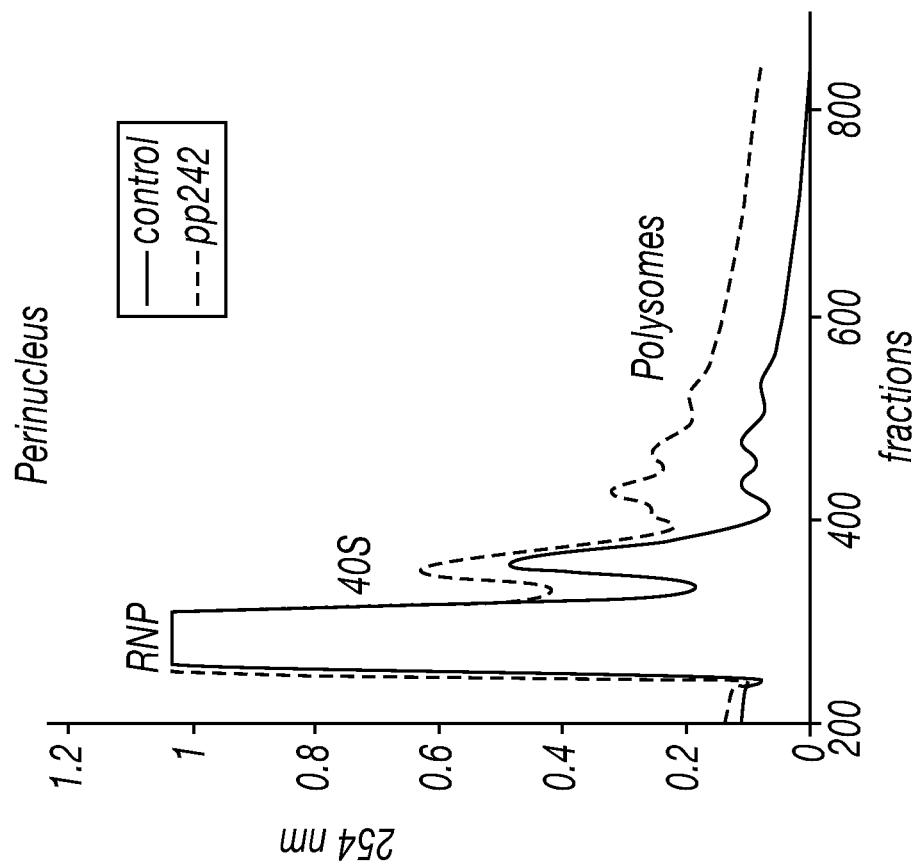
FIG. 3 is a graph of the cytoplasmic and the perinuclear polysome profiles of HCT-15 cells.
Figure 3A:
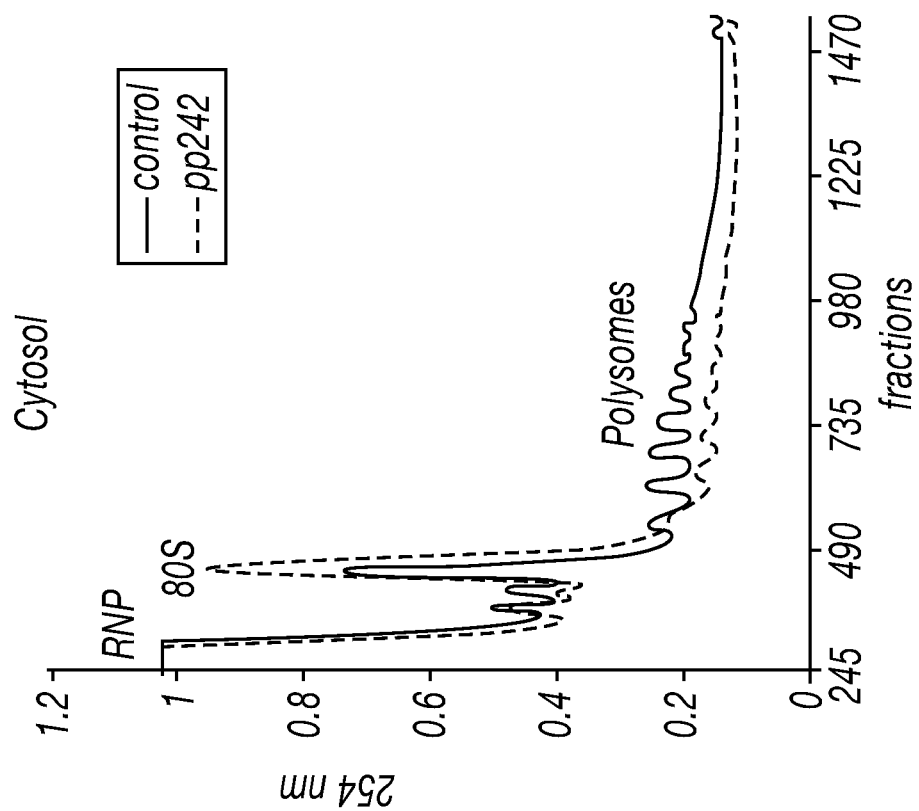

FIG. 3 shows the cytoplasmic and the perinuclear polysome profiles of HCT-15 cells in which differences between them include:

The different numbers of fractions in cytosol—1470 (A), in perinucleus—800 (B);

mTOR inhibitor, pp242, (red line) decreases the polysome level, increases the monosome (80S) level and decreases a large subunit (60S) level in the cytosol, relatively to the control (blue line), mTOR inhibitor, pp242, (red line) increases the polysome, the monosome (80S), and a large subunit (60S) levels in the perinucleus, relatively to the control (blue line).

Figure 4:
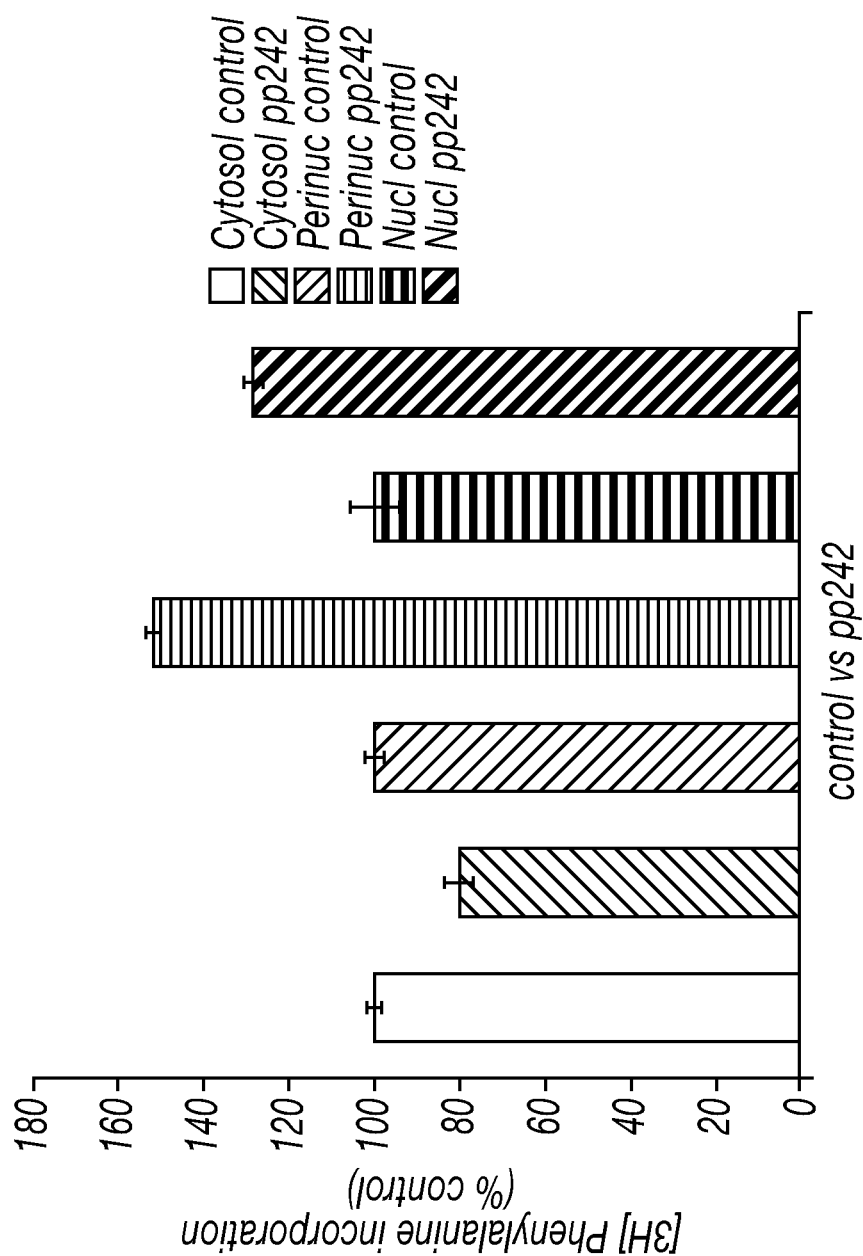
FIG. 4 is a graph of the incorporation of L-[$^3$H]-Phenylalanine into proteins of cytosol, perinucleus, and nucleus of HCT-15 cells.

FIG. 4 is a graph of the incorporation of L-[$^3$H]-Phenylalanine into proteins of cytosol, perinucleus, and nucleus. The suppression of protein synthesis by mTOR inhibitor pp242 decreased the incorporation of labeled phenylalanine by 20% in the cytosol but increases by 50% in perinucleus and by 30% in the nucleus relative to the control.

Figures 5A, 5B:
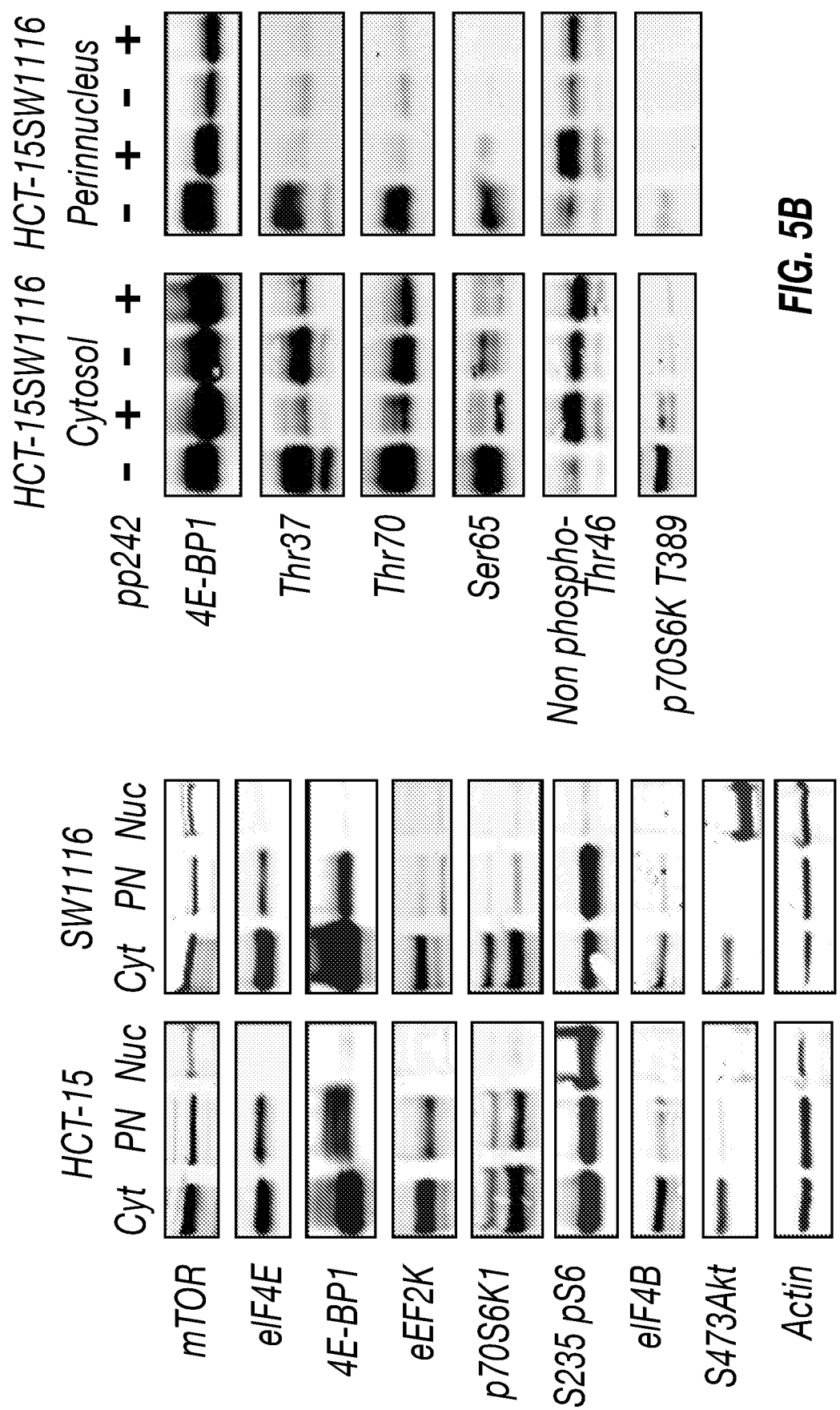
FIG. 5 is localization of mTOR and its substrates in the cytosol, perinucleus and nucleus and 4E-BP1 phosphorylation status in the cytosol and in the perinucleus.

FIG. 5 shows localization of mTOR and its substrates in the cytosol, perinucleus and nucleus and 4E-BP1 phosphorylation status in the cytosol and in the perinucleus in fast growing HCT-15 and extremely slow growing SW1116 colon adenocarcinoma cells.

HCT-15 contain in the perinucleus and the cytosol: mTOR, eIF4E, 4E-BP1, eEF2k, p70S6K1, but eIF4B is localized mostly in the cytosol (A).

SW1116 cells contain in the perinucleus and the cytosol: mTOR, eIF4E, 4E-BP1, but eEF2k, p70S6K1, eIF4B proteins localized mostly in cytosol (A).

In the cytosol and perinucleus phosphorylation of Tr37, Tr46, Tr70 and Ser 65 is inhibited by mTOR inhibitor pp242 in HCT-15 cells (B).

In the cytosol phosphorylation of Tr37, Tr46, Tr70 and Ser 65 is inhibited by mTOR inhibitor pp242 in SW1116 cells, but in the perinucleus, these amino acid sites were not phosphorylated at normal cell growth condition.

Figure 6B:
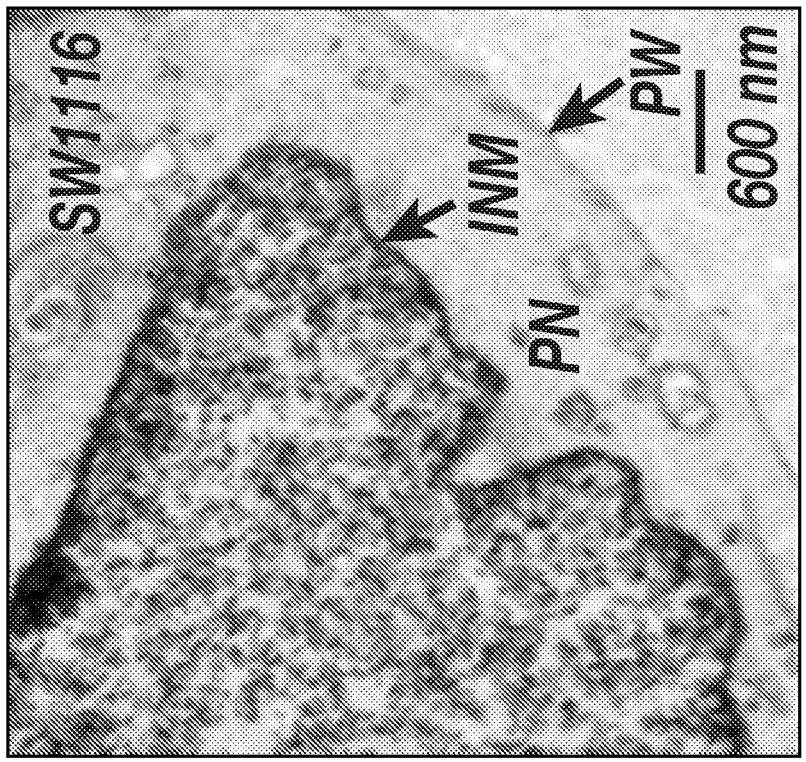
FIG. 6 contains transmission electron microscopy pictures of the perinucleus of fast-growing HCT-15 and extremely slow-growing SW1116 colon adenocarcinoma cells.
Figure 6A:
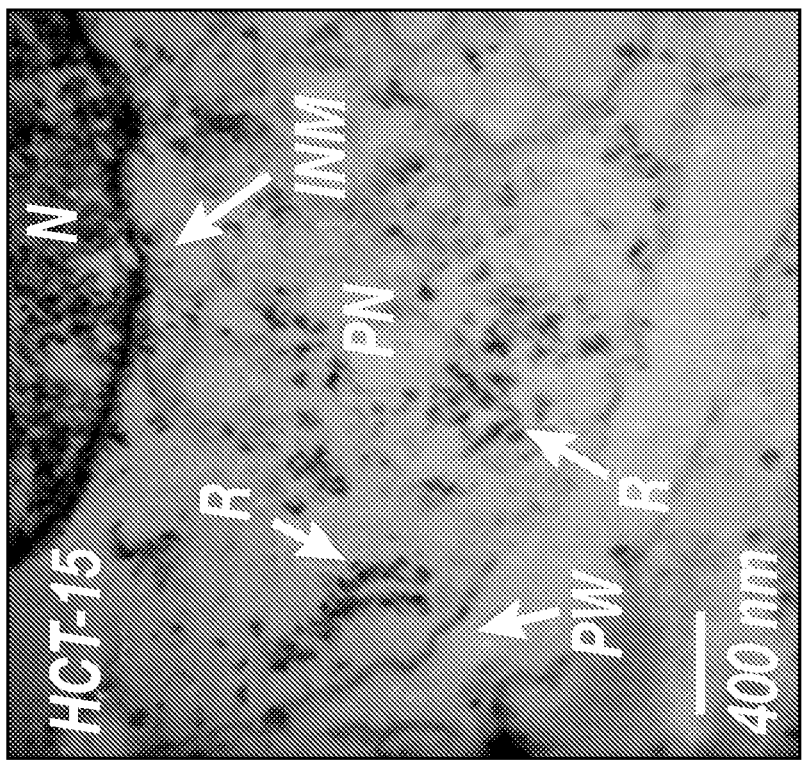

FIG. 6 contains transmission electron microscopy pictures of the perinucleus of fast-growing HCT-15 and extremely slow-growing SW1116 colon adenocarcinoma cells.

The perinucleus of HCT-15 cells were abundant with the ribosomal and polysomal particles The perinucleus of SW1116 cells were scarce with the ribosomal and polysomal particles.

Figure 8D:
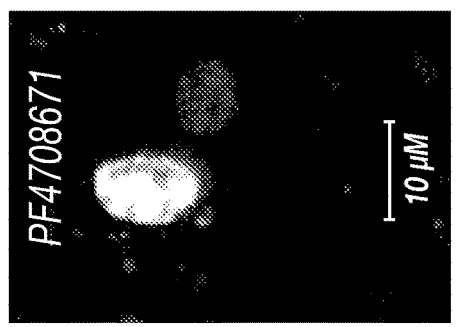
FIG. 8 contains photographs of GFP-L7a expression in untreated and treated HCT-15 cells.
Figure 8C:
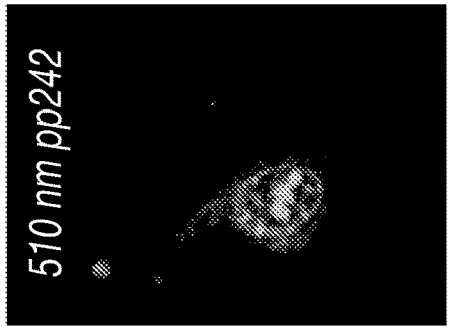

In Figure, R=ribosomes, PN=perinucleus; N=nucleus, INM=inner nuclear membrane; PW=perinuclear wall FIG. 8 contains pictures of cells. HCT-15 cells, grown on 35 mm glass bottom dishes, were transfected with the GFP-L7a vector pCMV6-AC-GFP to express GFP-L7a protein. GFP-L7a accumulated in the nucleolus of the cell (FIG. 8A).

Figure 8B:
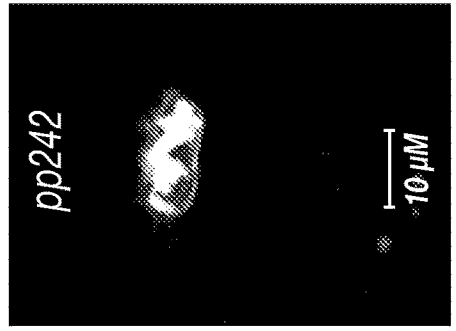
Figure 8A:
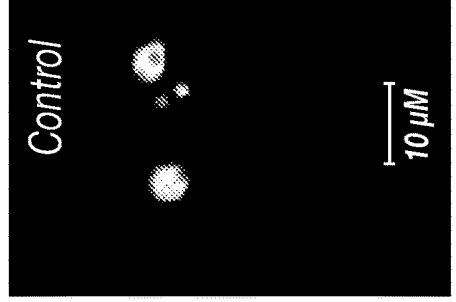

Testing compound pp242 induced perinuclear protein synthesis and nucleolar hypertrophy (FIG. 8B).

Spectral fingerprinting at 510 nm confirmed that the nuclear and perinuclear emission corresponded to GFP (FIG. 8C).

Compound PF4708671 induced perinuclear protein synthesis and nucleolar hypertrophy (FIG. 8D).

Figure 8H:
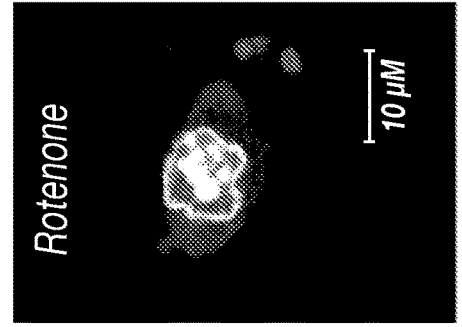
Figure 8G:
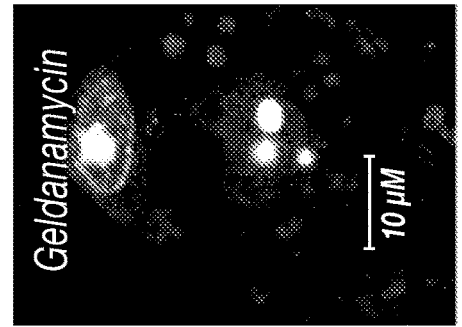
Figure 8F:
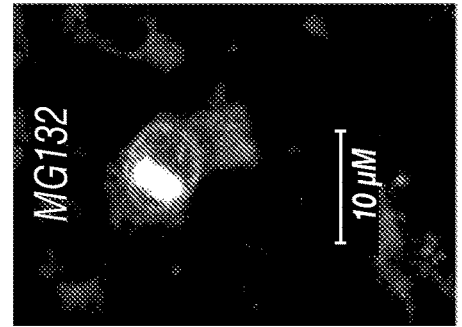
Figure 8E:
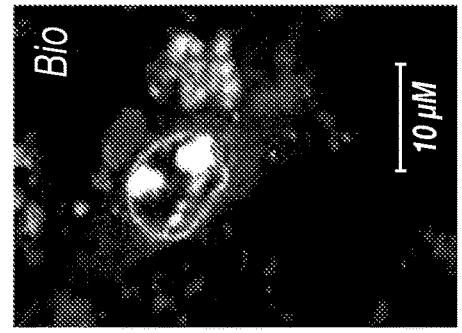

Compound Bio induced perinuclear protein synthesis and nucleolar hypertrophy (FIG. 8E).

Compound MG132 induced perinuclear protein synthesis and nucleolar hypertrophy (FIG. 8F).

Compound Geldanamycin induced perinuclear protein synthesis and nucleolar hypertrophy (FIG. 8G).

Compound Rotenone induced perinuclear protein synthesis and nucleolar hypertrophy (FIG. 8H).

Primary evidence shows that nucleolar hypertrophy depends on the perinuclear ribosomal protein synthesis.

What is claimed is:

1. A method for screening a cancer cell of a human subject for a nucleolar hypertrophy reducing agent comprising:
contacting an isolated cancer cell characterized by nucleolar hypertrophy with a first test sample; and
determining if the first test sample reduces the nucleolar hypertrophy in the isolated cancer cell.

2. The method of claim 1, wherein determining if the first test sample reduces the nucleolar hypertrophy in the isolated cancer cell comprises:
  measuring at least one of a decrease in a number of nucleoli, a number of nucleoli-containing nuclei, and a number of nucleoli per nucleus in the isolated cancer cell relative to the isolated cancer cell characterized by nucleolar hypertrophy before contact with the first test sample.

3. The method of claim 1, wherein determining if the first test sample reduces the nucleolar hypertrophy in the isolated cancer cell comprises:
  measuring at least one of a decrease in a number of nucleoli, a number of nucleoli-containing nuclei, and a number of nucleoli per nucleus relative to a control isolated cancer cell characterized by nucleolar hypertrophy.

4. The method of claim 1, further comprising:
  screening the cancer cell of the human subject for a nucleolar hypertrophy inducing agent comprising:
  contacting the isolated cancer cell with a second test sample; and
  determining if the second test sample induces nucleolar hypertrophy in the isolated cancer cell.

5. The method of claim 4, wherein determining if the second test sample induces nucleolar hypertrophy in the isolated cancer cell comprises:
  measuring at least one of an increase in a number of nucleoli, a number of nucleoli-containing nuclei, and a number of nucleoli per nucleus in the isolated cancer cell relative to the isolated cancer cell before contact with second test sample.

6. The method of claim 4, wherein determining if the second test sample induces nucleolar hypertrophy in the isolated cancer cell comprises:
  measuring at least one of an increase in a number of nucleoli, a number of nucleoli-containing nuclei, and a number of nucleoli per nucleus in the isolated cancer cell relative to a control isolated cancer cell.

7. The method of claim 4, wherein the second test sample includes a kinase inhibitor, a proteasome inhibitor, a protein inhibitor, an electron transport chain inhibitor, or a ribosomal inhibitor, or a combination thereof.

8. The method of claim 4, wherein the second test sample includes 2-(4-amino-1-isopropyl-1H-pyrazolo[3,4-d]pyrimidin-3-yl)-1H-indol-5-ol; 2-((4-(5-Ethylpyrimidin-4-yl)piperazin-1-yl)methyl)-5-(trifluoromethyl)-1H-benzo[d]imidazole; (2'Z,3'E)-6-Bromoindirubin-3'-oxime; (2R,6aS,12aS)-1,2,6,6a,12,12a-hexahydro-2-isopropenyl-8,9-dimethoxychromeno[3,4-b]furo(2,3-h)chromen-6-one; Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate; or (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate; or a combination thereof.

9. The method of claim 4, wherein an increase of from about 50% to about 400% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected.

10. The method of claim 4, wherein an increase of from about 150% to about 400% of at least one of an increase in a number of nucleoli, a number of nucleoli-containing nuclei, and a number of nucleoli per nucleus in the isolated cancer cell relative to a control isolated cancer cell is detected.

11. The method of claim 1, where the first test sample comprises an FDA approved drug, a natural product, an alkaloid, a monoterpene, a sesquiterpene, a diterpene, a flavonoid, a macrolide, a polyphenol, an anthocyanin, a saponin, a lignin, a coumarin, a glucoside, a quinine, an antimetabolite, an anthracycline, an antibiotic, a steroid, an inorganic compound, an organic compound, or a combination thereof.

12. The method of claim 1, wherein the first test sample includes the second test sample and at least one of a FDA approved drug, a natural product, an organic compound, an inorganic compound or a combination thereof.

13. The method of claim 1, wherein a decrease of from about 10% to about 80% of at least one of a number of nucleoli, a number of nucleoli-containing nuclei, and a number of nucleoli per nucleus in the isolated cancer cell relative to the isolated cancer cell characterized by nucleolar hypertrophy before contact with the first test sample is detected.

14. The method of claim 1, wherein a decrease of from about 10% to about 80% of at least one of a decrease in a number of nucleoli, a number of nucleoli-containing nuclei, and a number of nucleoli per nucleus relative to a control isolated cancer cell characterized by nucleolar hypertrophy is detected.

15. The method of claim 1, wherein the isolated cancer cells are selected from the group consisting of HCT-15, AGS, MDA-MB-231, MDA-MB-435, HeLa, HepG2, normal fibroblasts, and a sample from a cancer patient.

* * * * *